(12) United States Patent
Betti

(10) Patent No.: US 7,348,020 B1
(45) Date of Patent: Mar. 25, 2008

(54) INVASIVE MEDICAL DEVICE, ESPECIALLY FOR GUIDED TISSUE REGENERATION

(75) Inventor: Vittorio Betti, Faenza (IT)

(73) Assignee: Ghimas S.p.A., Casalecchio Di Reno (IT)

( * ) Notice: Subject to any disclaimer, the term of this patent is extended or adjusted under 35 U.S.C. 154(b) by 951 days.

(21) Appl. No.: 10/130,022

(22) PCT Filed: Oct. 23, 2000

(86) PCT No.: PCT/EP00/10413

§ 371 (c)(1),
(2), (4) Date: Apr. 19, 2002

(87) PCT Pub. No.: WO01/30409

PCT Pub. Date: May 3, 2001

(30) Foreign Application Priority Data

Oct. 25, 1999 (IT) .............................. BO99A0571

(51) Int. Cl.
*A61F 13/00* (2006.01)
*A61F 2/00* (2006.01)
*A61K 31/715* (2006.01)

(52) U.S. Cl. ...................... 424/422; 424/423; 424/426; 514/59

(58) Field of Classification Search ................ 424/422, 424/423, 426, 400; 514/59
See application file for complete search history.

(56) References Cited

U.S. PATENT DOCUMENTS 5,492,697 A * 2/1996 Boyan et al. ............. 623/16.11
5,679,723 A 10/1997 Cooper et al. ............... 523/115
6,530,958 B1 * 3/2003 Cima et al. ............... 623/23.51

FOREIGN PATENT DOCUMENTS

| DE | 19805673 | 8/1999 |
|----|----------|--------|
| EP | 0700671 | 3/1996 |
| WO | WO9825653 | 6/1998 |
| WO | WO9902201 | 1/1999 |
| WO | WO9919003 | 4/1999 |
| WO | WO0045870 | 8/2000 |

* cited by examiner

*Primary Examiner*—Johann R. Richter
*Assistant Examiner*—Konata M. George
(74) *Attorney, Agent, or Firm*—Richard M. Goldberg

(57) ABSTRACT

Biodegradable invasive medical device, in particular for guided tissue regeneration, which device comprises a biodegradable polymer, composed of a thermoplastic and/or thermosetting polymer admixed to a solvent that is miscible with any aqueous and/or aqueous alcoholic and/or alcohol-group-containing solution and/or with physiological liquids, whether of a synthetic or natural type. The said water-insoluble thermoplastic and/or thermosetting polymer and the water-miscible solvent for the polymer and mixed together in such a proportion as to form an organogel or a plastigel or a xerogel, or a solid-containing pasty product of the slurry type.

32 Claims, No Drawings

INVASIVE MEDICAL DEVICE, ESPECIALLY FOR GUIDED TISSUE REGENERATION

BACKGROUND OF THE INVENTION

The present invention relates to a biodegradable invasive medical device, especially for tissue regeneration, which device comprises a biodegradable polymer, composed of a thermoplastic and/or thermosetting polymer, mixed with one or more solvents, which solvents are miscible with water and/or with any aqueous and/or aqueous alcoholic and/or alcohol-group-containing solution, and/or with physiological liquids, whether of a synthetic or natural type.

Polymers of this type are already known and are currently widely used for tissue regeneration and specifically for the regeneration of bony and ligamentous tissues in general, and in particular periodontal tissues in periodontal pockets.

For example, European Patent No. 0,484,387 describes a polymer of this type, in which the mixture of the thermoplastic polymer and the solvent is in liquid form, so that it can be applied by injection with a syringe fitted with a needle.

When the liquid mixture has been injected, the water or the physiological liquid acts to wash away the solvent, while the polymer, which is insoluble in water, forms a porous filling that can be penetrated by solvated proteins and salts, followed by the cells that will regenerate the tissues.

A notable disadvantage of the known biodegradable polymer is that the application as a liquid solution cannot be easily contained and confined to a given site, especially when the zone of application does not have any fixed boundaries. The liquid spreads in an uncontrolled manner, reaching positions or sites where its presence is undesirable.

U.S. Pat. No. 5,487,897 relates to a similar polymer in the form of a bag with a containing outside wall that is relatively hard but still mouldable, and which has the mixture of thermoplastic polymer and solvent in a substantially liquid state inside it. The aim of this object is to solve the problem of confining the use of the polymer in liquid form. On the one hand, this does ensure the containment of the core of the liquid in the bag, but on the other hand the formation of the bag, which also consists of a biodegradable polymer, requires a complicated process and cannot be done easily by medical personnel. There is no effective way of checking the success of the operation involved in the preparation of the bag, and the results are therefore far from being guaranteed, not to mention the manual skill needed, the loss of time, and the need to observe the times and conditions of the preparation.

Another disadvantage of the polymers according to the prior art described in the documents mentioned above is that the liquid and the bag containing it must be washed away completely by the physiological liquid in order to eliminate the solvent. The washing-away naturally starts at the outer surface of the implanted mass and then advances progressively towards the centre of the implant. Relatively long periods of time are therefore needed to ensure the washing-away of the whole volume of the implanted polymer and solvent solution, and hence the complete hardening of the polymer mass. In addition, the solidifying outer layers reduce the speed at which the physiological liquids penetrate the inside of the implanted polymer mass.

SUMMARY OF THE INVENTION

The aim of the present invention is therefore to provide an invasive medical device, especially for tissue regeneration as described above, which retains the advantages of the known devices but makes it possible to avoid their disadvantages in an efficient manner.

Another aim of the invention is to improve the device described above, so as to make it possible to use it even in fields of application in which the current devices have been found unsuitable.

These aims are achieved according to the present invention with the aid of an invasive medical device, especially for tissue regeneration, in which the water-insoluble thermoplastic and/or thermosetting polymer and the solvent that is intended for this polymer and which is miscible with water are mixed together in such a proportion that contains 15-40 wt-% of the polymer and 50-70 wt-% of the solvent so as to form an organogel or a so-called plastigel or a xerogel, or else a solid-containing paste of the slurry type.

The term "organogel" is used here to describe any form of organic gel consisting of macromolecular substances.

The term "plastigel" is used to describe a particular type of organic gel consisting especially of thixotropic macromolecular substance.

The term "xerogel" is used to describe a porous material that can absorb a liquid giving rise to swelling phenomena known as capillary swelling (see Enciclopedia della Chimica ["Encyclopaedia of Chemistry"], vol. VI., published by USES, Florence, 1997, pages 61-64).

The viscosity lies in the range from $6.6 \times 10^{15}$ cP to 131.6 cP, measured at a temperature of 46° C. and is in any case such that the said mixture can be placed in position with a piston-and-cylinder type compressive system, or a pneumatic, mechanical or magnetic system, such as for example a syringe without a needle, or an extrusion device.

The highly viscous slurry-like state can be obtained by preparing the solution with a higher percentage of thermoplastic and/or thermosetting polymer than that corresponding to the saturation level either in the warm or in the cold state, and/or by admixing to the thermoplastic and/or thermosetting polymer and to the solvent a certain amount of water and/or aqueous and/or aqueous alcoholic and/or alcohol-group-containing solution and/or physiological liquids in such a way that the mixture is in any case substantially homogeneous as regards both the percentages of its components and its consistency over the whole cross section of the mass of material.

For an advantageous embodiment of the mixture of biodegradable thermoplastic and/or thermosetting polymers with suitable solvents and possibly also water, it is possible to add solid or high-viscosity substances to improve the mechanical properties, the ability to form an interface with cells, and a guided regeneration of bone. The materials to be added can be chosen from amongst homologous synthetic macromolecular substances such as polylactic acid or polyglycolic acid having various molecular weights or synthetic polymers that are biocompatible. These additives can be incorporated in amounts of 5-95%, calculated on the total composition.

Materials of a biological origin have also been found to be advantageous, such as autologous and/or heterologous and/or natural and/or fixed and/or demineralized or deproteinated or chemically immuno-masked human bone, and/or cartilage and/or dura mater, whether these are natural, fixed or lyophilized, autologous or not, as well as such substances derived from non-human mammals. Also suitable are some substances of inorganic origin or substances made inorganic by thermal and/or chemical and/or enzymatic means, such as coral, hydroxyapatite, sulphates, inert oxides, disperse metals, graphite and carbon derivatives obtained by pyrolysis, together with plastics. These substances can also be added in amounts of 5-95%, calculated on the total composition. Solid mixtures of synthetic macromolecular substances and the biological or inorganic substances mentioned above are also advantageous and can be added in the same amounts.

The additives combined with the thermoplastic and/or thermosetting polymer mass can in particular be in the form of particles ranging in shape from scale-like to spherical, via the irregular polyhedral, their dimensions being between 0.1 micron and 3000 microns.

The additives can also be materials obtained by the rough comminution of sponges made of biodegradable solid homologous thermoplastic and/or thermosetting polymers, these sponges being formed by a mixture of the polymer and e.g. dextran dispersed in a solvent, which solvent is then removed by a physical process, such as lyophilization (freeze-drying), for example.

In particular, the additive to the thermoplastic and/or thermosetting polymer can be a powder structured with dextran and a homologous polymer and used either in the industrial form or prepared extempore at the moment of use.

Examples of comminuted solids made from sponges are alginates, collagen, cartilagin, chondroitin sulphates, hyaluronic acid, acrylic and methacrylic sponges, platinum metal sponges and noble metal sponges. These additives are considered to improve the biodegradable plastigel polymer.

As regards the slurry form containing various additives, the use of a plastigel-slurry is claimed here as a desirable means for the formation of intercalated layered applications of the solids mentioned above.

In particular, the following substances are claimed here: layers of xerogels formed by plastigels of a lactic/co-glycolic polymer or a lactic or glycolic polymer or polycaprolactone or polyanhydrides or polyamides or polyurethane or polyesteramides or polyorthoesters or polydioxanone or polyacetal or polyketal or polycarbonate or polyorthocarbonate or polyphosphazene or polyhydroxybutyrate or polyhydroxyvalerate or polyalkylene oxalate or polyalkylene succinate or poly(maleic acid) or polyamino acids or polyvinylpyrrolidone or polyethylene glycols or polyhydroxycellulose or chitin or chitosan, and copolymers, terpolymers (with optionally organized solids), whether organic or not, with mixtures of the same, whether or not of human origin and whether or not of a natural or a derived mineral type.

These methods make it possible to obtain a shorter degradation time, a better hold and/or a better mechanical performance, together with a more efficient interface between the device and the cells.

According to an advantageous embodiment, biocompatible additives, and in particular those which increases the viscosity and/or improve the mechanical performance and/or the ability to perform a guided tissue regeneration, can be added later to the pasty mixture of the biodegradable thermoplastic and/or thermosetting polymer the solvent, possibly together with water and/or an aqueous and/or aqueous alcoholic and/or an alcohol-group-containing solution and/or physiological liquids.

It is possible in particular to admix during the preparation of the product a certain amount of variously fine granulate of the thermoplastic and/or thermosetting polymer and/or autologous or heterologous human and/or animal bone and/or cartilage, dura mater, fixed and/or natural collagens and/or synthetic and/or natural inorganic derivatives. It is advantageous in this case if the thermoplastic and/or thermosetting polymer is mixed with water, which triggers off its microprecipitation.

As an alternative to this and/or in combination with this, it is possible to admix the following substances to the mixture of biodegradable thermoplastic and/or thermosetting polymer and the solvent: organic or inorganic materials in powder and/or fragmented and/or granular form, such as granules and/or fragments and/or powders of suitably treated human and/or animal bony tissue and inorganic derivatives such as hydroxyapatite and/or bio-glass and/or coral and/or gypsum and/or plastics.

As an alternative to and/or in combination with the above, it is possible to add to the mixture suitably shaped small pieces and/or granules of a solid material in sponge form prepared from the said biodegradable thermoplastic and/or thermosetting polymer and a solvent, as well as from an excipient such as dextran for example, or from materials of organic and/or inorganic origin, such as for example small pieces of suitably treated human or animal bony tissue, as well as from inorganic derivatives, such as for example small pieces of hydroxyapatite and/or bio-glass and/or coral and/or gypsum and/or plastics.

In this case, the mixture of the biodegradable polymer, the solvent and dextran is dried, so that the dextran forms an open-cell structure that traps the solvent and polymer molecules in its cavities.

Owing to all these possible mixtures, not only a greater plasticity and/or rigidity can be ensured but also, particularly in the case of polymers applied in the liquid form, there is an improvement in the mechanical strength, i.e. in the resistance of the device to deformation between the time of placing the device in position and its hardening, total degradation and/or replacement.

Owing to its mechanical properties, the device according to the invention can be used in a plurality of applications in which polymers cannot be used currently, because they are applied in the liquid form.

The reason for this is that the mass of the implant is less easily deformed, in particular because of the use of small pieces of the dried mixture in sponge form and/or as granules of suitably treated human and/or animal bony tissues, as well as inorganic derivatives such as hydroxyapatite and/or bio-glass and/or coral and/or gypsum and/or plastics, since these have a substantially rigid form.

It is also possible to place the implant device in position extempore as a composite structure or form in which layers of the dried mixture in sponge and/or granular and/or powder form alternate with layers of the mixture in the form of an organogel, and especially a plastigel or xerogel, or else a slurry.

Owing to the granules and/or powders of suitably treated human and/or animal bony tissue, as well as of inorganic derivatives like hydroxyapatite and/or bio-glass and/or coral and/or gypsum and/or plastics, it is possible to reduce the mass of the material in the form of a pasty mixture such as an organogel, plastigel, xerogel, slurry and similar products, especially in the central area of the volume occupied by the said mass of material, and thereby reduce the hardening time of the device, while also promoting its biocompatibility and/or biodegradation.

The thermoplastic polymer that can be used may be any biodegradable polymer currently known to be biocapatible and in particular those chosen from the following groups: polylactides, polyglycolides, polycaprolactones, polyanhydrides, polyamides, polyurethanes, polyesteramides, polyortho esters, polydioxanones, polyacetals, polyketals, polycarbonates, polyorthocarbonates, polyphosphazenes, polyhydroxybutyrates, polyhydroxyvalerates, polyalkylene oxalates, polyalkylene succinates, poly(maleic acid), polyamino acids, polyvinylpyrrolidones, polyethylene glycols, polyhydroxycellulose, chitin, chitosan, and copolymers, terpolymers and/or combinations and/or mixtures of these substances. The following compounds can be used as solvents of these macromolecular substances: N-methyl-2-pyrrolidone, 2-pyrrolidone, ethanol, propylene glycol, acetone, methyl acetate, ethyl acetate, ethyl lactate, methyl ethyl ketone, dimethylformamide, dimethyl sulphone, tetrahydrofuran, caprolactam, decyl methyl sulphoxide, oleic acid, ethyl oleate, N,N-diethyl-m-toluamide, 1-dodecylazacycloheptan-2-one and/or mixtures of these substances.

The invention also relates to the use of an invasive medical device of the above type for the preparation of a device for tissue growth, particularly for the growth of bony tissue in the maxillary sinus.

With the explosive development of the techniques of implantation in recent years there has been a great advance from the clinical and scientific points of view in the growth of bony tissue in the maxillary sinus, where the thickness of the bone at one's disposal is of fundamental importance, since this thickness can sometimes be too small to ensure the application and the stability of the implant. The numerous surgical techniques developed in the field of implants are based on the assumption that the osseous structures in the maxillary sinus posses the ability to form new bone from the walls and particularly from the floor of the sinus itself.

The fact is that the "on-lay" techniques practised on the crest and the grafts of autologous bone inside the cavity of the sinus have both a series of advantages (in particular the presence of growth factors and absolute compatibility) and a series of disadvantages (mainly the more or less pronounced resorption of the graft and hence an uncertainty about the size). Of the numerous techniques used, Caldwell-Luc's anterolateral fenestration, with the elevation of the sinus and successive filling, is currently the most often used technique. It has the advantages that it is relatively easy to perform, permits a good visual control of the filling operation, and makes it possible to predict the result if synthetic materials are used. However, its drawbacks are not negligible either. Thus, it involves a marked invasion for the patient, a great risk of mucosal perforation, and the danger of infectious sinusitis.

This technique is well known and therefore will not be described here.

A new technique has also been used recently, which is characterized by a very low degree of invasiveness with a great elevation of the floor of the maxillary sinus for implantation purposes. It has a series of advantages, namely a very low degree of invasiveness, very good predictability of the dimensions, a drastic reduction of the risk of perforating the mucosa, a shorter surgical time needed, less suffering for the patient during the operation and in the postoperative period, and less time needed for the formation of new bone. This surgical technique involves a small cristal incision and separation over the whole thickness to display the top of the osseous crest corresponding to the floor of the sinus, and the creation of one or more holes with a diameter of 3.8 mm according to the number of implants to be inserted, these holes running from the top of the crest to the floor of the maxillary sinus that is to be broken through. The patient's autologous bone, for example, is then inserted into these holes.

The present invention proposes an improvement of this technique for a small or a large elevation of the sinus by replacing e.g. the patient's autologous bone by a biodegradable polymer in the form of an organogel, in particular a plastigel or xerogel, or else a slurry. The tip of a syringe without a needle, or an extrusion device containing the biodegradable biopolymer in the form of an organogel, plastigel, xerogel, slurry or the like is inserted with precision into the holes mentioned above. After checking that the mucosa inside the sinus is intact (negative Valsalva test), the material in question is injected into the cavity of the sinus at a constant, low pressure. The material in question may be a biodegradable polymer in the form of a plastigel, slurry or xerogel, used either by itself or mixed with the polymer sponge in powder and/or granule form and/or as small pieces, and/or with powders and/or granules and/or small pieces of a biological material, such as small pieces of autologous or heterologous human and/or animal bony tissue, and/or cartilage, dura mater, natural and/or fixed collagen, and/or synthetic and/or natural inorganic derivatives, as well as inorganic derivatives such as hydroxyapatite and/or bio-glass and/or coral and/or gypsum and/or plastics. In particular, the slurry or a similar material by itself raises the mucosa in the sinus in a completely atraumatic manner and stabilizes it, thus forming a space in which the organization of the osteoid coagulum can take place between the osseous floor and the membrane. This coagulum later develops into newly formed bony tissue, thereby raising the floor.

The invention also relates to the use of the biodegradable thermoplastic and/or thermosetting polymer for the preparation of an invasive implant device for tissue regeneration in artificial fractures created by bone distraction in general, and in the distraction of the upper and/or lower jaw bone, in particular.

In this case, the two parts of the fractured bone are separated from each other, and into the zone of fracture is applied the mixture of a biodegradable polymer and the powders, granules or small pieces of polymer sponge and/or the biological tissue, such as pieces of suitably treated human and/or animal bony tissue, as well as the inorganic derivatives such as hydroxyapatite and/or bio-glass and/or coral and/or gypsum and/or plastics.

The present invention also relates to the use of the biodegradable polymer for the preparation of an invasive implant device for tissue regeneration in the supplementation of bone or cartilage, such as for example in cosmetic and other forms of surgery and in post-traumatic therapeutic maxillofacial interventions, and in interventions involving the elevation of the alveolar crest, including such interventions carried out for cosmetic reasons.

The present invention also relates to the use of the biodegradable polymer for the preparation of an invasive implant device for tissue regeneration in the bone or cartilage supplementation, such as for example in the field of otorhinolaryngology when reconstructing the mega-cavity after open tympanoplastic interventions and in the reconstruction of the osseous nasal pyramid in traumatic or iatrogenic cases.

The present invention also relates to the use of the biodegradable polymer for the preparation of an invasive implant device for tissue regeneration in bone supplementation in the orthopaedic field, such as for example in the removal of osseous cysts, in surgical interventions of vertebral arthrodesis, and for the improvement of the integration of hip and femur replacements with the bones, and generally in all cases of fracture gaps where the ends do not meet precisely.

The present invention also relates to the use of the biodegradable polymer for the preparation of an invasive implant device for tissue regeneration in bone supplementation in the neurological field, such as for example in the case of bone ablations from the resected skull that are necessary for the removal of pathological parts of the brain and meninges, especially in the case of osteolysis.

The present invention also relates to the use of the invasive implant device for the preparation of a device for the regeneration of other types of tissues that are not necessarily rigid, such as for example in corrective urological surgery.

The embodiments of the invention are described in the sub-claims.

DETAILED DESCRIPTION

The invasive medical implant device is prepared by the method described below.

The mixture of the meltable component (the polymer) and the melting aid (PEG) is melted together in a suitable container made of glass, metal, plastic or another suitable material, with stirring and in a current of an inert gas.

The melting temperature should in particular lie in the range between +12° C. and +239° C., and in particular between +48° C. and +150° C.

The stirring should be done with a propeller-type stirrer that does not create a vortex and is operated at a speed of between 30 and 180 rpm; at least four-fifths of the volume of the screw end of the stirrer should be immersed in the mixture.

The inert-gas flow should not generate a bubbling stream and should not have a flow rate in excess of 1 liter per minute.

The melting aids (a mixture of PEG 400, PEG 600 and PEG 1500) should be liquid and homogeneous before the immersion of the polymer (50:50 lactic/co-glycolic polymer).

The 50:50 lactic/co-glycolic polymer should be in the form of a fine powder with a particle size not exceeding 70-80 microns.

The polymer should be added, using the upper orifice of the reactor (container) employed for the mixing operation. The polymer weighed out should be added slowly, with minimum stirring (30 rpm).

After the addition of the polymer, the stirrer speed is brought to 120 rpm, and the temperature of the mixture is adjusted to 75±1° C.

The temperature of the mixture should be kept constant, with the aid of a water bath, throughout the time needed for the complete melting of the polymer (about 3.5 hours).

An inert gas (e.g. nitrogen) should be passed in throughout this time at a rate of about 1 liter per minute.

When the solubilization is complete, the temperature of the molten mass is reduced to 55° C. The necessary amount of distilled water is added while maintaining this temperature and flow of inert gas.

At this point, the stirrer speed used for the mixing is raised to 180 rpm.

When the appearance of the mass changes from a clear amber colour to an opaque amber colour, the lowering of the temperature to room temperature is started while keeping the flow rate of nitrogen or another inert gas constant.

This step is essential for ensuring that a homogeneous slurry is obtained.

The entire process and the equipment used for it should be characterized by a reduced bacterial count, which should not be higher than 10 colony forming units [lacuna].

The product is placed in 1-ml single-dose dispensers, using 500 mg of the product at a time.

The product is packed in small anti-tear plastic bags and sterilized with gamma rays for 72 hours.

The actual percentages of the materials are as follows:

| | | |
|---|---|---|
| 50:50 lactic/co-glycolic polymer | 300 g | (30%) |
| PEG 400 | 300 g | (30%) |
| PEG 600 | 200 g | (20%) |
| PEG 1500 | 190 g | (19%) |
| Distilled water | 10 g | (1%) |

The percentage by weight can vary within the following range at a temperature of 20° C.

| | Minimum | Maximum |
|---|---|---|
| 50:50 PLA/co-PGA polymer | 1% | 90% |
| PEG 400 | 1% | 90% |
| PEG 600 | 1% | 90% |
| PEG 1200 | 20% | 60% |
| Distilled water | 1% | 90% |

The consistency of the resulting mixture is that of an organogel and in particular a plastigel or xerogel, or it is a solid-containing paste of the slurry type or a similar product. It can be used by itself as such and/or it can be mixed with small pieces and/or powders and/or granules of the same biodegradable polymer (in the form of sponges or a pulverized sponge material), or else with small pieces or granules of biological or inorganic tissue, such as for example bony tissue or soft tissue like cartilage, dura mater, and natural or fixed collagen.

The granules or small pieces will have different particle sizes, depending on the type of application. When the material is applied with a compressive applicator, the granules or small pieces that may be added should obviously have a particle size and shape that make it possible for them to pass freely through the outlet orifice of the applicator.

The biodegradable polymer in sponge form can be obtained as described below.

The right amount of steam-distilled water and the right amount of F.U. dextran are placed in a suitable container made of glass, metal or plastic.

When the dextran has been solubilized, the whole solution is passed through a sterile filter with a pore size of 2 microns, and the filtrate is collected in a sterile beaker.

The lactic/glycolic copolymer, taken out of its protective packaging, should be reduced to particles measuring 80-125 microns.

This is done by grinding the polymer mass in a suitable manual grinder, characterized by a reduced bacterial count of 2 c.f.u./cm$^2$ of the grinder discs, the grinding being carried out under a Class 100 laminar-flow hood.

The polymer powder is incorporated in the dextran solution in an immersion-type homogenizer operated at a speed of 5000 rpm for 2 minutes, without the use of vortex screws.

A number of casting moulds make of teflon-coated aluminium are cleaned with RPE acetone.

The mass is poured into the moulds.

The moulds with the material in them are subjected to rapid freezing, so that they are frozen in 15 minutes at most.

A lyophilizing cycle is carried out, giving a residual final moisture content of at most 2%.

At the end of the lyophilizing cycle, the moulds are turned upside-down, and the sponges formed in them are collected in a two-liter beaker.

A teflon-coated heating plate is warmed up under a laminar-flow hood.

RPE acetone is added to the sponges in the beaker in an amount that can be absorbed by them.

The sponges are quickly transferred to the heating plate warmed to 40° C. under a Class 100 laminar-flow hood.

The material is assumed to be ready after 2.5 hours.

The material, each piece of which weighs 183 mg, is packed singly in sealed dappen and inserted into plastic bags.

The material is sterilized with gamma rays for 72 hours.

The actual percentages of the materials are as follows:

| | |
|---|---|
| 50:50 lactic/co-glycolic polymer: | 53 g |
| K70 dextran | 135 g |
| Distilled water | 500 g |

The percentages by weight can vary within the following range at a temperature of 20° C.

| | Minimum | Maximum |
|---|---|---|
| 50:50 PLA/co-PGA polymer | 1% | 90% |
| K70 dextran | 1% | 90% |
| Distilled water | 1% | 90% |

The following examples serve to explain the present invention in more detail but the latter is not limited to them.

Example 1

An invasive medical device for tissue regeneration is used to obtain a growth of the maxillary bone in the area of the maxillary sinus.

In this case, a biodegradable polymer in slurry form is used, to which are admixed homogeneously some small pieces of the biodegradable polymer in sponge form. The hole of application, which passes through the maxillary bone, can have a size of the order of several millimeters. The applicator can be a syringe-type device without a needle and with or without a rigid or soft cannula having a lumen of 0.1-30 mm, and in particular 1-3 mm, in the outlet orifice.

The small pieces of sponge or the sponge granules have sizes varying from 1 micron to 30 microns.

These are homogeneously admixed to the slurry and are present in an amount of 5-95% of the weight of the total mass of the implant.

The mixture formed by the biodegradable polymer in slurry form and the small pieces is applied under pressure to the site between the epithelial tissue of the bone and the bone itself until reaching the desired thickness or volume for the supplementation.

The device according to the invention is therefore particularly indicated for raising the floor of the maxillary sinus, whether by a small or large amount. The fact is that its consistency has been found to be sufficient to dislocate the Schneiderian membrane and to stay in place. This is achieved in a perfectly atraumatic way, thanks to the plasticity of the product. According to the new technique, characterized by minimum invasion, the gel or better still, gel slurry, makes it possible to achieve a large elevation of the sinal floor if injected directly into the sinal cavity through a hole whose diameter corresponds to the outlet orifice of the syringe. Once the opening hole has been made with a suitable instrument (while avoiding the laceration of the membrane), a smooth probe can be used to start the elevation and stabilization of the mucosa itself and the stabilization of a coagulum, which—originating in the focus of the bone fracture and in the laceration of the periosteum—quickly develops into new bony tissue. The device according to the invention efficiently maintains a real space in which the organization of the osteoid coagulum can take place.

It can be noted that, in this case, the presence of the small pieces or granules of polymer in sponge form or the biological or inorganic tissue increases the form retention characteristics of the implant mixture and reduces any differences between the volume of the implant itself and that of the regenerated tissue, thereby permitting more precise operation, owing to the greater correspondence in shape and size.

Example 2

In a case similar to that described in the previous example, the mixture of biodegradable polymer is slurry form to which small pieces of the biodegradable polymer in sponge form are admixed homogeneously is applied with an applicator such as for example a syringe without a needle, or an extrusion device. The material is inserted into the opening of one or more holes (depending on the number of implants to be inserted) having a diameter of 3.8 mm and running from the top of the crest to the floor of the maxillary sinus that is to be broken through. The surgical technique consists in making a small cristal incision, and a separation across the whole thickness to display the top of the osseous crest corresponding to the floor of the sinus.

Example 3

In a case similar to that described in the previous examples, the granules or small pieces admixed to the biodegradable polymer in slurry form are granules or small pieces of bony tissue and/or cartilage and/or dura mater and/or natural or fixed collagen.

Example 4

In a case similar to that described in the previous example, the small pieces or granules are a mixture of small pieces or granules of the biodegradable polymer in sponge form and small pieces or granules of the biodegradable polymer and biological tissue, such as for example bone and/or cartilage and/or dura mater and/or natural or fixed collagen.

Example 5

A biodegradable polymer in slurry form, possibly mixed with granules of biological or inorganic tissues, such as for example bony tissue is interposed between the layers of a similar biodegradable polymer in sponge form, in order to form a wafer structure.

Example 6

The product described in Examples 3-5 can be used in a nose remodelling operation to supplement bony tissue that is missing as a result of injury or disease or from birth. Such remodelling can be carried out by separating the nasal cartilage and introducing the biodegradable polymer in the above form between the cartilage itself and the nasal bone until the required packing volume is reached, followed by the juxtaposition of the cartilage, and the suturing of the surface layers.

Example 7

As in Example 6, the biodegradable polymer can be used in urology for plastic surgery inside or outside the urethra, following surgery on the prostate gland and/or on the bladder.

Example 8

An invasive medical device for tissue regeneration as in one or more of the previous examples is interposed between the two parts of a broken lower jaw bone. The two parts of the lower jaw are kept apart and/or held in a staggered position with a suitable distracting device.

Example 9

A biodegradable polymer in the form described in Examples 3-5 can be used similarly to the way described in Example 2 for the reintegration of the pulpy nucleus of degenerated intervertebral discs. In this case, the intervertebral bodies involved are kept apart in a stable manner, e.g. by plate fixation. The pulpal cavity is filled with the above polymer to achieve the ankylosis of the vertebral bodies involved.

In the above examples, the use of the invasive medical device according to the invention has been found to permit a regeneration in 1-9 months, i.e. in a relatively short time.

The combined use of the biodegradable polymer in slurry form and in sponge form, mixed with each other, or as layers and/or small pieces or granules of biological tissue does not only guarantee better mechanical characteristics of form retention and a better agreement between the mass of implant and the regenerated tissue, but it also makes it possible to avoid the considerable inconvenience to which patients are currently submitted, in particular in the supplementation of the maxillary bone in the area of the maxillary sinus and in plastic surgery on the nose. This is because, in the present case, it is not necessary to remove any bone or cartilage from another part of the patient's body.

What is claimed is:

1. A biodegradable invasive medical device for guided tissue regeneration, which device comprises:
    a biodegradable polymer that is comprised of at least one material selected from the group consisting of a water-insoluble thermoplastic and a thermosetting polymer admixed to a solvent that is miscible with
    at least one liquid selected from the group consisting of any aqueous solution, aqueous alcoholic solution, alcohol-group-containing solution and synthetic or natural physiological liquids,
    the at least one material selected from the group consisting of a water-insoluble thermoplastic and thermosetting polymer and the liquid-miscible solvent for the polymer are mixed in such a proportion that contains 15-40 wt-% of the polymer and 50-70 wt-% of the solvent so as to form a mixture selected from the group consisting of an organogel, a plastigel, a xerogel, and a solid-containing pasty material,
    wherein the mixture contains the at least one material selected from the group consisting of a water-insoluble thermoplastic and thermosetting polymer in a percentage that is higher than that corresponding to a saturation level, and
    wherein the device further contains 0.1-70 wt-% of the at least one liquid selected from the group consisting of any aqueous solution, aqueous alcoholic solution, alcohol-group-containing solution and synthetic or natural physiological liquids,
    wherein biocompatible additives which increase the viscosity, increase mechanical performance and/or improve tissue regeneration and bone regeneration are added to the mixture that is in a form selected from the group consisting of an organogel, plastigel, xerogel and slurry and is formed between the at least one material selected from the group consisting of a thermoplastic and thermosetting biodegradable polymer and the solvent, and
    said additives include at least one material selected from the group consisting of powders, granules, and small pieces of material with a spongy consistency and consisting of at least one of the thermoplastic and thermosetting polymer, and
    the following components are mixed together:
    0.5-97 wt-% of at least one material selected from the group consisting of a powder, granules, and small pieces of a material with a spongy consistency and consisting of at least one of the thermoplastic and thermosetting polymer, and
    dextran.

2. The device according to claim 1, wherein the viscosity of the mixture lies in the range from $6.6 \times 10^{15}$ cP to 131.6 cP, measured at a temperature of 46° C. and is such that said mixture can be placed in position with a piston-and-cylinder compressive system including a syringe without a needle.

3. The device according to claim 1, wherein the at least one material of at least one of the thermoplastic and thermosetting polymer selected from the group consisting of a powder, granules and small pieces of a material with a spongy consistency, is admixed to an excipient.

4. The device according to claim 1, wherein 1-9 wt-% of the at least one material selected from the group consisting of a water-insoluble thermoplastic and a thermosetting polymer is mixed with 10-90 wt-% of an excipient.

5. The device according to claim 1, wherein material of biological origin are admixed to the mixture of the at least one material selected from the group consisting of a biodegradable thermoplastic and thermosetting polymer and the solvent.

6. A biodegradable invasive medical device for guided tissue regeneration, which device comprises:
    a biodegradable polymer that is comprised of at least one material selected from the group consisting of a water-insoluble thermoplastic and a thermosetting polymer admixed to a solvent that is miscible with
    at least one liquid selected from the group consisting of any aqueous solution, aqueous alcoholic solution, alcohol-group-containing solution and synethetic or natural physiological liquids,
    the at least one material selected from the group consisting of a water-insoluble thermoplastic and thermosetting polymer and the liquid-miscible solvent for the polymer are mixed in such a proportion that contains 15-40 wt-% of the polymer and 50-70 wt-% of the solvent so as to form a mixture selected from the group consisting of an organogel, a plastigel, a xerogel, and a solid-containing pasty material, and
    suitably shaped small pieces and/or granules of a solid material of a sponge form prepared from said biodegradable polymer and the solvent, together with an excipient which are admixed to the device that is in the form of a mixture selected from the group consisting of an organogel, a plastigel, a xerogel, and a slurry.

7. The device according to claim 6, wherein the sponge form has an open-cell structure, formed by molecules of the at least one material selected from the group consisting of a thermoplastic and a thermosetting polymer, and the dried dextran.

8. The device according to claim 7, wherein the mixture is further comprised of at least one of the following:
at least one material selected from the group consisting of small pieces, granules and powders of the thermoplastic and/or thermosetting polymer in sponge form, and
at least one material selected from the group consisting of small pieces, granules and powders of tissues, and biological materials.

9. A biodegradable invasive medical device for guided tissue regeneration, which device comprises:
a biodegradable polymer that is comprised of at least one material selected from the group consisting of a water-insoluble thermoplastic and a thermosetting polymer admixed to a solvent that is miscible with
at least one liquid selected from the group consisting of any aqueous solution, aqueous alcoholic solution, alcohol-group-containing solution and synethetic or natural physiological liquids,
the at least one material selected from the group consisting of a water-insoluble thermoplastic and thermosetting polymer and the liquid-miscible solvent for the polymer are mixed in such a proportion that contains 15-40 wt-% of the polymer and 50-70 wt-% of the solvent so as to form a mixture selected from the group consisting of an organogel, a plastigel, a xerogel, and a solid-containing pasty material,
wherein the device has a structure of an essentially laminated composite material with alternating layers of the biodegradable polymer in sponge form and layers of the biodegradable polymer in the form of a mixture with the polymer solvent.

10. The device according to claim 1, wherein the material selected from the group consisting of a thermoplastic and thermosetting polymer includes any of existing biodegradable polymers that are currently known to be biocompatible, and which are chosen from the group consisting of polylactides, polyglycolides, polycaprolactones, polyanhydrides, polyamide, polyurethane, polyesteramides, polyortho esters, polydioxanones, polyacetals, polyketals, polycarbonates, polyorthocarbonates, polyphosphazenes, polyhydroxybutyrates, polyydroxyvaleates, polyalkylene oxalate, polyalkylene succinates, poly(maleic acid), polyamino acids, polyvinylpyrrolidone, polyethylene glycols; polyhydroxycellulose, chitin, chitosan, and copolymers, terpolymers and/or combinations and/or mixtures of the above materials.

11. The device according to claim 1, wherein the solvent is selected from the group consisting of N-methyl-2-pyrrolidone, 2-pyrrolidone, ethanol, propylene glycol, acetone, methyl acetate, ethyl acetate, ethyl lactate, methyl ethyl ketone, dimethylformamide, dimethyl sulphone, tetrahydrofuran, caprolactam, decal methyl sulphoxide, oleic acid, ethyl oleate, N,N-diethel-m-toluamide, 1-dodecylazacycloheptan-2-one and/or mixtures of these substances.

12. The device according to claim 6, wherein said device is used for the growth of bony tissue in the maxillary sinus.

13. The device according to claim 6, wherein said device is used for tissue regeneration in artificial fractures created by bone distraction.

14. The device according to claim 6, wherein said device is used for tissue regeneration in remodeling interventions in plastic nose surgery with bone supplementation.

15. The device according to claim 6, wherein said device is used for the regeneration of types of tissues that are not necessarily rigid.

16. The device according to claim 6, wherein said device is used for tissue regeneration in plastic surgery inside or outside the urethra.

17. The device according to claim 6, wherein said device is used for tissue regeneration connected with the supplementation of bone or cartilage.

18. The device according to claim 6, wherein said device is used for tissue regeneration in bone or cartilage supplementation.

19. The device according to claim 6, wherein said device is used for tissue regeneration in bone supplementation in the orthopaedic field.

20. The device according to claim 6, wherein said device is used for tissue regeneration in bone supplementation in the neurological field.

21. The device according to claim 1, wherein the mixture contains the at least one material selected from the group consisting of a water-insoluble thermoplastic and thermosetting polymer in a percentage that is higher than that corresponding to a saturation level.

22. A biodegradable invasive medical device for guided tissue regeneration, which device comprises:
a biodegradable polymer that is comprised of at least one material selected from the group consisting of a water-insoluble thermoplastic and a thermosetting polymer admixed to a solvent that is miscible with
at least one liquid selected from the group consisting of any aqueous solution, aqueous alcoholic solution, alcohol-group-containing solution and synthetic or natural physiological liquids,
the at least one material selected from the group consisting of a water-insoluble thermoplastic and thermosetting polymer and the liquid-miscible solvent for the polymer are mixed in such a proportion that contains 15-40 wt-% of the polymer and 50-70 wt-% of the solvent so as to form a mixture selected from the group consisting of an organogel, a plastigel, a xerogel, and a solid-containing pasty material,
wherein the mixture contains the at least one material selected from the group consisting of a water-insoluble thermoplastic and thermosetting polymer in a percentage that is higher than that corresponding to a saturation level, and
wherein the device further contains 0.1-70 wt-% of the at least one liquid selected from the group consisting of any aqueous solution, aqueous alcoholic solution, alcohol-group-containing solution and synthetic or natural physiological liquids, and
the device further contains 1-25 wt-% of the liquid selected from the group consisting of any aqueous solution, aqueous alcoholic solution, alcohol-group-containing solution and synthetic or natural physiological liquids.

23. The device according to claim 6, wherein
the at least one material of at least one of the thermoplastic and thermosetting polymer is selected from the group consisting of a powder, granules and small pieces of a material with a spongy consistency,
is admixed to dextran as an excipient, and
wherein biocompatible additives which increase the viscosity, increase mechanical performance and/or improve tissue regeneration and bone regeneration are added to the mixture that is in a form selected from the group consisting of an organogel, plastigel, xerogel and slurry and is formed between the at least one material selected from the group consisting of a thermoplastic and thermosetting biodegradable polymer and the solvent, said additives including at least one material selected from the group consisting of powders, granules, and small pieces of material with a spongy consistency and consisting of at least one of the thermoplastic and thermosetting polymer.

24. A biodegradable invasive medical device for guided tissue regeneration, which device comprises:
   a biodegradable polymer that is comprised of at least one material selected from the group consisting of a water-insoluble thermoplastic and a thermosetting polymer admixed to a solvent that is miscible with
   at least one liquid selected from the group consisting of any aqueous solution, aqueous alcoholic solution, alcohol-group-containing solution and synthetic or natural physiological liquids,
   the at least one material selected from the group consisting of a water-insoluble thermoplastic and thermosetting polymer and the liquid-miscible solvent for the polymer are mixed in such a proportion that contains 15-40 wt-% of the polymer and 50-70 wt-% of the solvent so as to form a mixture selected from the group consisting of an organogel, a plastigel, a xerogel, and a solid-containing pasty material,
   wherein the mixture contains the at least one material selected from the group consisting of a water-insoluble thermoplastic and thermosetting polymer in a percentage that is higher than that corresponding to a saturation level, and
   wherein the device further contains 0.1-70 wt-% of the at least one liquid selected from the group consisting of any aqueous solution, aqueous alcoholic solution, alcohol-group-containing solution and synthetic or natural physiological liquids,
   wherein 1-9 wt-% of the at least one material selected from the group consisting of a water-insoluble thermoplastic and a thermosetting polymer is mixed with 10-90 wt-% of an excipient, and
   wherein the excipient is dextran.

25. A biodegradable invasive medical device for guided tissue regeneration, which device comprises:
   a biodegradable polymer that is comprised of at least one material selected from the group consisting of a water-insoluble thermoplastic and a thermosetting polymer admixed to a solvent that is miscible with
   at least one liquid selected from the group consisting of any aqueous solution, aqueous alcoholic solution, alcohol-group-containing solution and synthetic or natural physiological liquids,
   the at least one material selected from the group consisting of a water-insoluble thermoplastic and thermosetting polymer and the liquid-miscible solvent for the polymer are mixed in such a proportion that contains 15-40 wt-% of the polymer and 50-70 wt-% of the solvent so as to form a mixture selected from the group consisting of an organogel, a plastigel, a xerogel, and a solid-containing pasty material,
   wherein the mixture contains the at least one material selected from the group consisting of a water-insoluble thermoplastic and thermosetting polymer in a percentage that is higher than that corresponding to a saturation level, and
   wherein the device further contains 0.1-70 wt-% of the at least one liquid selected from the group consisting of any aqueous solution, aqueous alcoholic solution, alcohol-group-containing solution and synthetic or natural physiological liquids,
   wherein materials of biological origin are admixed to the mixture of the at least one material selected from the group consisting of a biodegradable thermoplastic and thermosetting polymer and the solvent, and
   wherein said materials of biological origin include materials selected from the group consisting of human bone that may be autologous and/or heterologous, natural or fixed, demineralized or deproteinated or chemically immuno-masked, cartilage and/or dura mater, whether natural, fixed or lyophilized, autologous or not, as well as, substances of inorganic origin or substances made inorganic by thermal and/or chemical and/or enzymatic means, including coral, hydroxyapatite, sulphate, inert oxides, disperse metals, graphite obtained by pyrolysis, together with plastics.

26. The device according to claim 9, wherein the mixture of layers of the biodegradable polymer includes a precipitant selected from the group consisting of an aqueous solution, an aqueous alcoholic solution, an alcohol-group-containing solution and synthetic or natural physiological liquids, in a form selected from the group consisting of an organogel, a plastigel, a xerogel and a slurry.

27. The device according to claim 6, wherein said device is used in the distraction of the lower jaw bone.

28. The device according to claim 6, wherein said device is used in the reintegration of the pulpy nucleus in degenerated or arthrosic intravertebral discs.

29. The device according to claim 6, wherein said device is used in cosmetic and other forms of surgery and in post-traumatic therapeutic maxillofacial interventions and in interventions involving the elevation of the alveolar crest, including such interventions carried out for cosmetic reasons.

30. The device according to claim 6, wherein said device is used for tissue regeneration in bone or cartilage supplementation, and
   wherein said device is used in the field of otorhinolaryngology when reconstructing the mega-cavity after open tympanoplastic interventions and in the reconstruction of the osseous nasal pyramid in traumatic or iatrogenic cases.

31. The device according to claim 6, wherein said device is used in the removal of osseous cysts, in surgical interventions of vertebral arthrodesis, and for the improvement of the integration of hip and femur replacements with the bones, and generally in all cases of fracture gaps where the ends do not meet precisely.

32. The device according to claim 6, wherein said device is used in the case of bone ablations from the resected skull that are necessary for the removal of pathological parts of the brain and the meninges, especially in the case of osteolysis.

* * * * *